US00PP20440P3

(12) United States Plant Patent
Whetman

(10) Patent No.: US PP20,440 P3
(45) Date of Patent: Oct. 27, 2009

(54) *DIANTHUS* PLANT NAMED 'WP PASSION'

(50) Latin Name: *Dianthus×hybrida*
Varietal Denomination: WP Passion

(76) Inventor: John Whetman, Deerpark Farm, Churdleigh, Newton Abbey, Devon (GB) TQ13 0NH ( * ) Notice: Subject to any disclaimer, the term of this patent is extended or adjusted under 35 U.S.C. 154(b) by 5 days.

(21) Appl. No.: 12/220,573

(22) Filed: Jul. 24, 2008

(65) Prior Publication Data

US 2009/0031463 P1 Jan. 29, 2009

(51) Int. Cl.
*A01H 5/00* (2006.01)

(52) U.S. Cl. ..... Plt./283

(58) Field of Classification Search ..... Plt./273, Plt./283

See application file for complete search history.

*Primary Examiner*—Susan B McCormick Ewoldt

(57) ABSTRACT

A new cultivar of *Dianthus* plant named 'WP PASSION' that is characterized by pronounced compact habit, grey-green foliage, and large deep red double flowers. In combination these traits set 'WP PASSION' apart from all other existing varieties of *Dianthus* known to the inventor.

2 Drawing Sheets

Genus: *DIANTHUS*

Species: *×hybrida*

Denomination: 'WP PASSION'

BACKGROUND OF THE INVENTION

This application claims the benefit of priority under 35 U.S.C. 119(f) of the earlier application for European Plant Breeders Rights, Application Number 2007/1881 filed Jul. 26, 2007.

The present invention relates to a new and distinct cultivar of *Dianthus* that is grown for use as a flowering plant for pots and containers and as a hardy perennial for the garden and landscape. The new cultivar is known botanically as *Dianthus×hybrida* and will be referred to hereinafter by the cultivar name 'WP PASSION'.

'WP PASSION' is a complex hybrid plant that is the product of a long term breeding program conducted in a greenhouse environment in Houndspool, Dawlish, Devon, United Kingdom. The primary focus of the breeding program is to produce new cultivars of *Dianthus* that exhibit unique growth habit and colors. The inventor selected 'WP PASSION' in 2003 for its large, dark red, double flowers, compact habit, and grey-green foliage.

'WP PASSION' resulted from the controlled between *Dianthus* code name '96-02' as female parent, and *Dianthus* code name '94-21' as male parent. Both parents have been raised by the inventor and retained as breeding parents for their red flowers. Neither parent has been released or patented.

'WP PASSION' is distinguishable from both of parents by the vibrancy and intensity of its red flowers which the inventor considers to be so far unmatched amongst *Dianthus* of his origination or known in commerce.

The variety of *Dianthus* which is considered by the inventor to most closely resemble 'WP PASSION' is *Dianthus* 'Devon General' (unpatented). 'Devon General' has crimson flowers and grayer foliage while 'WP PASSION' has deep red flowers.

Asexual reproduction of the new cultivar was first accomplished by the inventor in 2003 in a cultivated area of Houndspool, United Kingdom. The method of asexual propagation used was vegetative cuttings. Since that time the characteristics of the new cultivar have been determined stable and are reproduced true to type in successive generations.

SUMMARY OF THE INVENTION

The following traits have been repeatedly observed and represent the characteristics of the new *Dianthus* cultivar 'WP PASSION'. These traits in combination distinguish this cultivar from all other commercial varieties known to the inventor. 'WP PASSION' has not been tested under all possible conditions and phenotypic differences may be observed with variations in environmental, climatic and cultural conditions, however, without any variance in genotype.

1. *Dianthus* 'WP PASSION' exhibits a compact habit.
2. *Dianthus* 'WP PASSION' blooms profusely.
3. *Dianthus* 'WP PASSION' exhibits flowers that are a deep red from February through October.
4. *Dianthus* 'WP PASSION' exhibits grey-green foliage.
5. At maturity, the height of the foliage mound of Dianthus 'WP PASSION' is 30 cm to 35 cm; the width is 20 cm to 25 cm.
6. *Dianthus* 'WP PASSION' is perennial and is hardy to −15° C.
7. *Dianthus* 'WP PASSION' is suitable for use as a flowering plant in pots and containers.

BRIEF DESCRIPTION OF THE DRAWINGS

The accompanying color drawings illustrate the overall appearance of the new *Dianthus* variety 'WP PASSION' showing colors as true as it is reasonably possible to obtain in colored reproductions of this type. Colors in the drawings may differ from the color values cited in the detailed botanical description, which accurately describe the actual colors of the new variety 'WP PASSION'.

The drawing labeled as FIG. 1 depicts an entire flowering plant.

Figure 1:
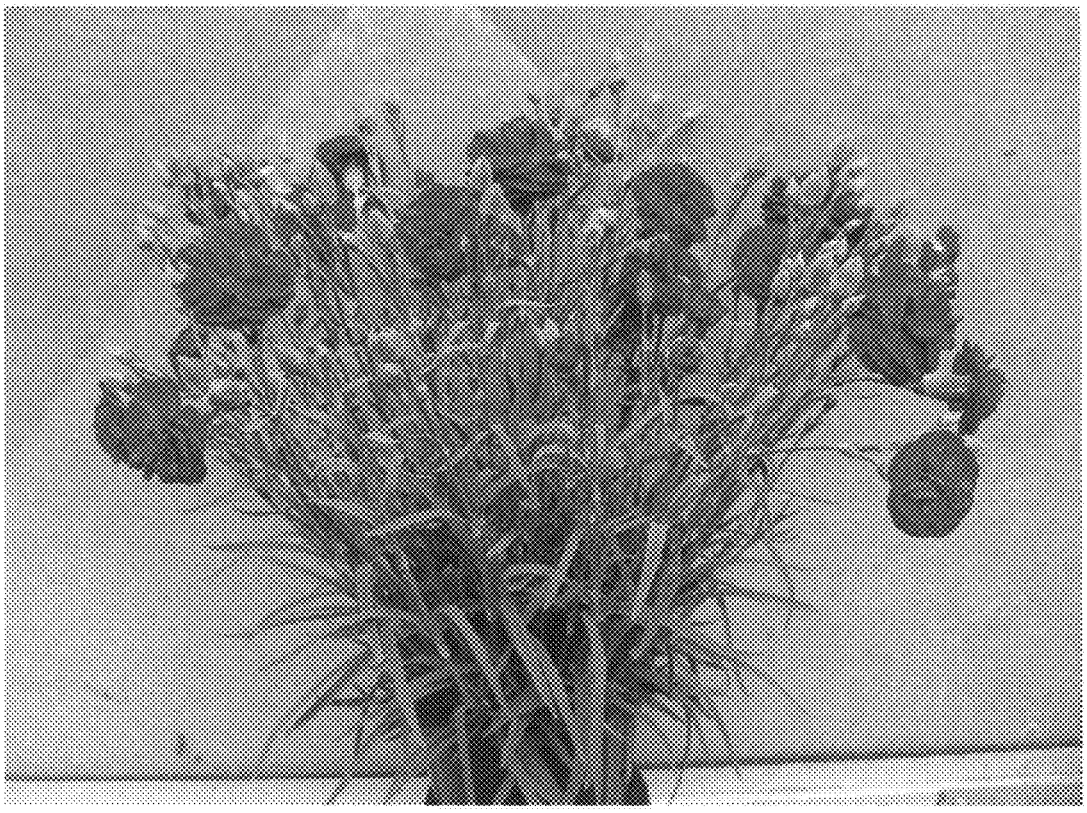
Figure 2:
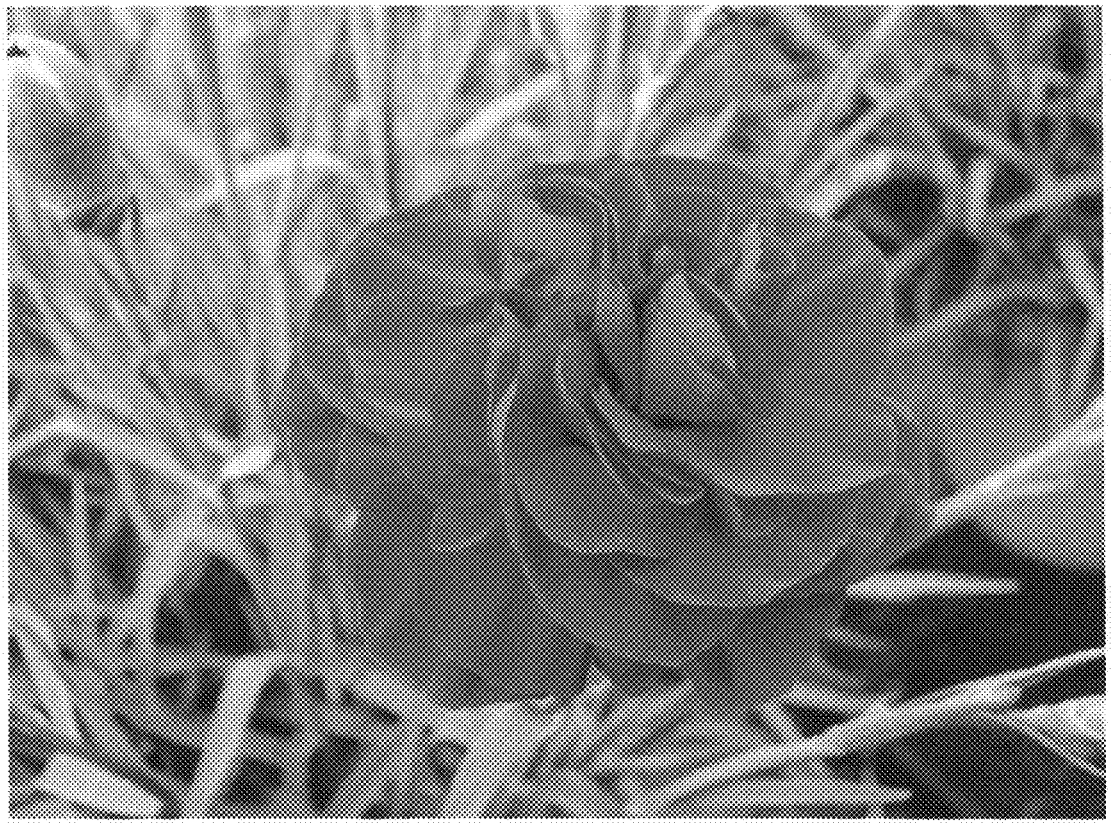

The drawing labeled as FIG. 2 depicts a close-up view of the flower.

All drawings were made of plants grown in 1.5-liter containers in a cold glasshouse in Devon, United Kingdom. No chemicals were used to treat the plants. All drawings were made using conventional techniques and although colors may appear different from actual colors due to light reflectance they are as accurate as possible by conventional photography.

DETAILED BOTANICAL DESCRIPTION OF THE PLANT

The following is a detailed description of the new cultivar 'WP PASSION'. Data was collected in spring from 1.5-liter container plants in spring, and grown indoors in Devon, United Kingdom. The color determinations are in accordance with the 2002 edition of The Royal Horticultural Society Colour Chart of The Royal Horticultural Society, London, England, except where general color terms of ordinary dictionary significance are used. The colors of stems, leaves, calyx, and epicalyx have been noted on plants which retain the characteristic waxy bloom of *Dianthus*. No chemicals were used to treat the plants. Growing conditions are typical to other *Dianthus*.

Botanical classification: *Dianthus* 'WP PASSION'.

Species: ×*hybrida*.

Common name: Dwarf *Dianthus*.

Commercial classification: *Dianthus* hybrid.

Type: Perennial.

Use: Used as a flowering plant for pots and containers and for planting in the garden or landscape.

Parentage: 'WP PASSION' is a complex hybrid plant that resulted from the controlled pollination between the following parent plants:

*Female parent plant.*—*Dianthus* '96.02'.

*Male parent plant.*—*Dianthus* '94.21'.

Plant description:

*Bloom period.*—February through October.

*Plant habit.*—Compact mound with many branches and stems; upright growth.

*Plant height.*—30 cm to 35 cm after 9 months.

*Plant width.*—20 cm to 25 cm after 9 months.

*Plant hardiness.*—Hardy to minus 15° Centigrade.

*Root system.*—Fine fibrous roots.

*Propagation.*—Propagation is accomplished using vegetative cuttings.

*Cultural requirements.*—Grow in full sun, with moderate water, and well-drained moderately fertile soil. Remove dead flower heads to maintain flowering.

*Diseases and pests.*—Susceptible to known *Dianthus* pests and disease but no other susceptibilities to pests or disease are known to the inventor.

*Time and temperature needed to produce a rooted cutting.*—3 weeks are needed to produce roots on cuttings using a mist propagation unit with bottom heat of 21° Centigrade, and a minimum air temperature of 15° Centigrade.

*Crop time.*—3 months starting in the early spring through summer and 6 months starting in the fall is needed to produce a finished container size plant from a well-rooted cutting.

Stem:

*Shape.*—Cylindrical.

*Stem dimensions.*—10 cm to 14 cm in height and 3 mm in diameter.

*Stem surface.*—Glabrous and glaucous.

*Stem color.*—145C.

*Branching.*—Numerous shoots from the axils of the lower leaves.

*Internode length.*—10 mm to 15 mm between nodes.

*Node color.*—145C.

*Node dimensions.*—4 mm in length and 3 mm in diameter.

Foliage:

*Type.*—Evergreen.

*Shape.*—Linear and straight.

*Division.*—Simple.

*Apex.*—Acute.

*Base.*—Decurrent.

*Venation.*—Not Prominent.

*Margins.*—Entire.

*Attachment.*—Sheathing.

*Arrangement.*—Opposite or spiraling.

*Surfaces* (*adaxial and abaxial*).—Glaucous.

*Leaf dimensions.*—70 mm to 85 mm in length and 3 mm to 4 mm in width.

*Leaf color* (*adaxial and abaxial surfaces*).—Between 198A and 191A.

*Fragrance.*—Absent.

Flowers:

*Inflorescence.*—Cymose.

*Number of flowers per stem.*—From 3 to 5.

*Peduncle dimensions.*—170 mm to 200 mm in length and 3 mm in width.

*Peduncle strength.*—Erect.

*Peduncle color.*—189A.

*Flower development.*—In sequence from the uppermost bud.

*Flower type.*—Salviform, double and symmetrical.

*Flower shape.*—Circular.

*Flower profile.*—Reflexed.

*Flower dimensions.*—Including calyx): 37 mm in length and 40 mm in width.

*Fragrance.*—Medium.

*Petals.*—Number: 20–30 petals. Profile, upper part of corolla: Convex. Profile, lower part of corolla: Concave. Arrangement: Persistent, double, apopetalous, overlapping. Margin: Entire to sinuate. Texture: Soft. Shape: Obdeltoid. Surface: Glabrous. Dimensions: 35 mm to 40 mm in length and 18 mm to 22 mm in width. Color (adaxial surface): Ground color of blade: Between 46A and 53A. Band across blade: No band. Middle of strap: 145C Base of strap: 145D. Color (abaxial surface): Ground color of blade: 63B. Band across blade: No band. Middle of strap: 145C. Base of strap: 145D.

*Calyx.*—Shape: Cylindrical Longitudinal profile: Flat. Dimensions: 20 mm to 25 mm in length and 8 mm to 10 mm in diameter. Sepals: Fused. Number of sepals: 5. Sepal color (both surfaces): 138A and 143C. Anthocyanin: Present only in the border. Splitting: Not observed.

*Epicalyx.*—Bracts: 1 pair of 2. Shape of outer lobe: Acuminate. Dimensions: 9 mm in length and 14 mm in width. Color: 136B on the tip and 144B on the blade. Anthocyanin: Not present.

*Bracteoles.*—Number: 2 Dimensions: 7 mm in length and 10 mm in width. Color: 136B on the tip and 144B on the blade. Anthocyanin: Not present.

*Lastingness of flower.*—Each individual flower lasts an average of 10 days at 20° C. on the plant.

Reproductive organs:

*Stamens.*—No true stamens, all are petaloid. 10–15' petaloid stamens present.

*Anthers.*—None.

*Pollen.*—Absent.

*Style.*—Number: 2 or 3. Shoulder: Absent. Color: NN155D. Dimensions: 15 mm to 25 mm in length and 1 mm in width.

*Stigma.*—Number: Single. Color: 59A. Dimensions: 3 mm to 5 mm above petals.

*Ovary.*—Position: Superior. Dimensions: 7 mm in length and 8 mm in diameter. Shape: Spindle. Color (adaxial): 144C. Color (abaxial): 145C.

*Seed.*—Number: 1–10. Dimensions: 3 mm in length and 2 mm in width. Color: 202A Shape: Oval and flattened. Surface: Crinkled.

What is claimed is:

1. A new and distinct cultivar of *Dianthus* plant named 'WP PASSION' as described and illustrated herein.

* * * * *